United States Patent [19]
Chang et al.

[11] Patent Number: 5,814,511
[45] Date of Patent: Sep. 29, 1998

[54] HUMAN BREAST EPITHELIAL CELL TYPE WITH STEM CELL AND LUMINAL EPITHELIAL CELL CHARACTERISTICS

[75] Inventors: Chia-Cheng Chang; James E. Trosko, both of Okemos, Mich.

[73] Assignee: Michigan State University, East Lansing, Mich.

[21] Appl. No.: 558,786

[22] Filed: Nov. 16, 1995

Related U.S. Application Data

[62] Division of Ser. No. 308,118, Sep. 16, 1994, Pat. No. 5,530,317.

[51] Int. Cl.$^6$ ..................................................... C12N 5/00
[52] U.S. Cl. .......................................................... 435/240.2
[58] Field of Search .......................................... 435/240.2

[56] References Cited

U.S. PATENT DOCUMENTS

| | | | |
|---|---|---|---|
| 4,411,990 | 10/1983 | Salmon et al. | 435/32 |
| 5,061,620 | 10/1991 | Tsukamoto et al. | 435/7.21 |
| 5,081,030 | 1/1992 | Civin | 435/240.2 |
| 5,087,570 | 2/1992 | Weissman et al. | 424/93.7 |
| 5,132,212 | 7/1992 | Kirsch et al. | 435/69.4 |
| 5,185,438 | 2/1993 | Lemischka | 536/23.2 |
| 5,214,133 | 5/1993 | Kirsch et al. | 530/399 |
| 5,226,914 | 7/1993 | Caplan et al. | 623/16 |
| 5,258,367 | 11/1993 | Bazer et al. | 514/6 |
| 5,270,458 | 12/1993 | Lemischka | 536/23.5 |
| 5,300,422 | 4/1994 | Gerson et al. | 435/4 |

OTHER PUBLICATIONS

"Contact Insensitivity of a Subpopulation of Normal Human fetal Kidney Epithelial Cells and of Human Carcinoma Cell Lines", Chang, et al, *Cancer Research 47*, pp. 1634–1645, Mar. 15, 1987.

*Primary Examiner*—John W. Rollins
*Attorney, Agent, or Firm*—Reising, Ethington, Barnard & Perry

[57] ABSTRACT

Described is a substantially purified human breast epithelial cell (Type I HBEC) displaying the following characteristics: variable cell shape; smooth cell colony boundary; deficiency in gap junctional intercellular communication; positive expression of epithelial membrane antigen and keratin 18; negative expression of keratin 14, α6 integrin and gap junction genes for connexins (Cx26, Cx32 and Cx43); growth promotion by fetal bovine serum; induction by cholera toxin to differentiate into Type II HBEC (prior art); and acquisition anchorage independent growth by Semian virus 40 transfection. Also described is a method of obtaining the above-identified epithelial cells comprising the steps of: a) development of a mixture of human breast epithelial cells from reduction mammoplasty tissues using the MSU-1 medium; b) eliminating stromal fibroblasts by a trypsin (0.002%) and ethylenediamine tetraacetic acid (0.02%) solution; c) separating Type I HBEC from Type II HBEC which attach on culture dishes earlier by collecting Type I HBEC that remain in suspension after trypsinization and prolonged incubation; d) the continuing culture of these cells in MSU-1 medium supplemented with fetal bovine serum, which inhibits the growth of Type II HBEC while promoting the growth of Type I HBEC, gives rise to Type I HBEC. Described also is a new defined medium (the MSU-1 medium) which supports the growth of both Type I and Type II human breast epithelial cells.

12 Claims, 7 Drawing Sheets

Type I

Type II

FIG. 5A  FIG. 5B
α6  β4
Type I
Type II
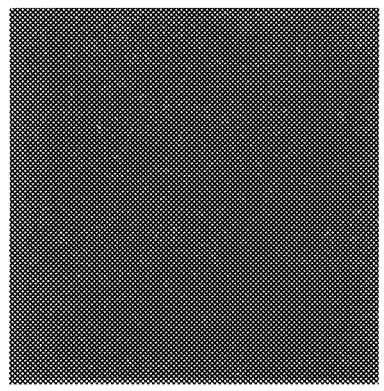
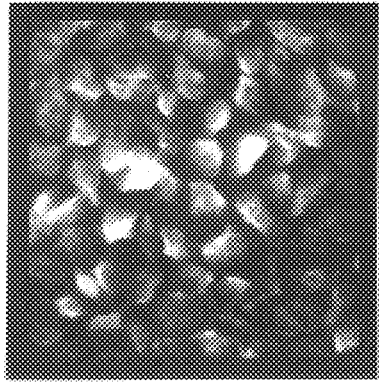
FIG. 5C  FIG. 5D

FIG. 6A     FIG. 6B
Type I
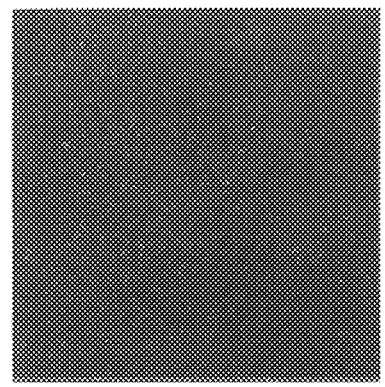 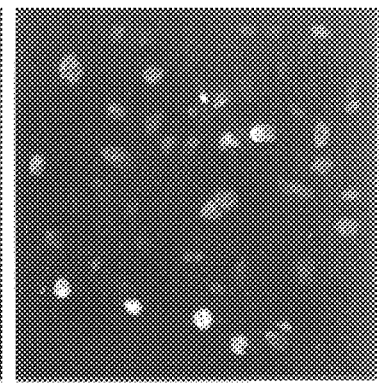
Type II
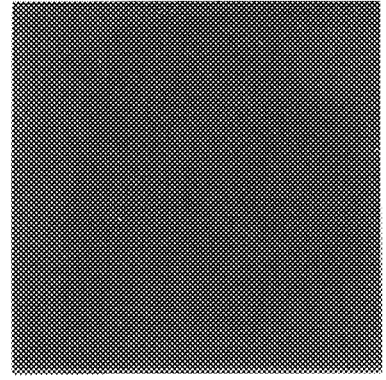 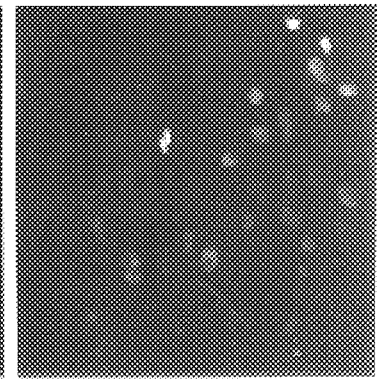
FIG. 6C     FIG. 6D

HUMAN BREAST EPITHELIAL CELL TYPE WITH STEM CELL AND LUMINAL EPITHELIAL CELL CHARACTERISTICS

This is a division of application Ser. No. 08/308,118 filed Sep. 16, 1994 now U.S. Pat. No. 5,650,317.

LICENSING RIGHTS

The United States government may have licensing rights under this invention as provided for in the National Institute of Health Research Grants CA 50430 and CA 21104.

TECHNICAL FIELD

The invention is directed toward epithelial cells and, in particular, human breast epithelial cells having stem cell characteristics.

BACKGROUND ART

The human breast contains a variety of cell types including luminal and basal epithelial cells that form the ductal tree. These two types of epithelial cells are immunocytochemically distinguishable in tissue sections (1) or in enzymatically dissociated single-cell suspensions (2). Antigenic markers that can distinguish these two cell types would include the epithelial membrane antigen (EMA) and keratin 18 which are predominantly expressed in luminal epithelial cells (1,2) and keratin 14 and $\alpha 6$ integrin which are specifically expressed in basal epithelial cells (1,3). When the expression of these antigenic markers were examined in primary human breast carcinomas, it was found that the carcinoma cells were similar to the luminal epithelial cells in their expression of antigens (1,3,4). This evidence can be interpreted as indicating that breast carcinomas are primarily derived from luminal epithelial cells or their precursor cells with similar phenotypes.

Most normal human breast epithelial cell cultures were derived either from lactational fluids, which contained cells primarily of luminal origin, or were derived from reduction mammoplasty. Cells from reduction mammoplasty, cultured in the commonly used MCDB 170 (Department of Molecular, Cellular and Developmental Biology, University of Colorado) (5) or DFCI-1 (Dana-Farber Cancer Institute) (6) media, exhibit predominantly basal epithelial cell phenotypes (1,4).

Stem cells are undifferentiated cells capable of (a) proliferation, (b) self-maintenance, (c) the production of a large number of differentiated, functional progeny, (d) regenerating the tissue after injury, and (e) a flexibility in the use of these options (37).

There is a strong interest in identifying the human hematopoietic stem cell. Having possession of the stem cell will allow for identification of growth factors associated with its self-regeneration. In addition, there may be as yet undiscovered growth factors associated (1) with the early steps of dedication of the stem cell to a particular lineage; (2) the prevention of such dedication; and (3) the negative control of stem cell proliferation. The availability of stem cells would be extremely useful in bone marrow transplantation, as well as transplantation of other organs or tissues (e.g., liver regeneration and skin grafting). Stem cells are important and ideal targets for gene therapy, where the inserted genes promote the health of the individual into whom the stem cells are transplanted since the stem cells have longer lifespan. In 1992, an Italian research group performed the first human gene transfer involving stem cells instead of lymphocytes in the hope of curing a 5 year old child with the rare genetic disease, adenosine deaminase deficiency. In addition, the ability to isolate the stem cell may serve in the treatment of Fanconi's anemia, Hodgkin's disease, lymphomas and leukemias (e.g., juvenile chronic myelogenous leukemia), as well as other neoplastic conditions (e.g., breast cancer). Thus, there have been world-wide efforts toward isolating the human hematopoietic stem cell in substantially pure or pure form. See U.S. Pat. No. 5,061,620, column 2, lines 3–22.

U.S. Pat. No. 4,411,990 describes a primary assay of human tumor stem cells. Example 1 discloses the treatment of bone marrow cells and their collection using an appropriate medium which contained fetal calf serum that have been inactivated by heat. The cells were suspended in additional horse serum, which contained antibiotics and various amino acids such as glutamine, asparagine, and the like. Column 10 notes that the application of simple in vitro culture technique for studies of human tumor stem cells from primary explants will prove of clinical importance.

U.S. Pat. No. 5,061,620 describes human hematopoietic stem cell, assigned to SyStemix, Inc. of California. Stem cells are separated from dedicated cells and they are maintained by regeneration in a growth medium. The separation is described in Columns 3 and 4 wherein monoclonal antibodies are useful for identifying markers associated with particular cell lineages and/or stages of differentiation. The antibodies may be attached to a solid support to allow for crude separation. Human stem cells are maintained in a medium for culturing the cells which is described in Column 5, Lines 57 and following which medium includes amino acids, vitamins, fetal calf serum and the like. Pluripotent human stem cell regeneration is discussed at Column 6, Lines 52 and following.

U.S. Pat. No. 5,081,030 describes release of cells from affinity matrices. Positive selection of normal marrow stem cells is performed utilizing a monoclonal antibody which selectively recognizes the progenitor cells.

U.S. Pat. No. 5,087,570 teaches a mammalian stem cell composition which is isolated with monoclonal antibodies. The antibodies are attached to a solid support to allow for separation.

U.S. Pat. No. 5,185,438 pertains to nucleic acids encoding stem cell receptor FLK-2. The patent pertains to methods of stimulating the proliferation of primitive mammalian hematopoietic stem cells comprising contacting the stem cells with a ligand that binds to a receptor protein tyrosine kinases expressed in primitive mammalian hematopoietic cells and not expressed in mature hematopoietic cells. A primitive hematopoietic cell is totipotent that is capable of reconstituting all hematopoietic blood cells in vivo. (Column 5, Lines 5–7) Column 8 and following describe the isolation of nucleic acid molecules and proteins that encode mammalian stem cell receptors. A source of stem cells includes fetal liver, spleen, or thymus cells or adult marrow or brain cells. Example 2 in Column 14 indicates a technique for isolating the stem cells from fetal liver. The separated re-suspended tissue is treated with heat-inactivated fetal bovine calf serum to inhibit trypsin activity. The tissue was resuspended in stromal medium which contains fetal calf serum, human serum, glutamine, sodium pyruvate, non-essential amino acids and a mixture of antibiotics. The sequences for various materials identified in the patent are shown. Similarly related is U.S. Pat. No. 5,270,458.

U.S. Pat. No. 5,214,133 teaches SCL, a hematopoietic growth and differentiation factor. SCL is a new human gene.

The SCL gene is of interest because it is involved with human stem cell leukemia.

U.S. Pat. No. 5,226,914 describes a method for treating connective tissue disorders. Culturing and passaging of marrow stromal cells are described in Column 9. The medium that was utilized included fetal bovine serum. A substantial list of medium components is described in Columns 5 and 6.

U.S. Pat. No. 5,258,367 is of interest in that it relates to utilizing uteroferrin and rose proteins for stimulating proliferation of hematopoietic cells.

U.S. Pat. No. 5,300,422 describes a screening method for controlling agranulocytosis. There the blood is collected and assayed for stem cell activity to N-desmethylclozapine. The stem cells are identified by specific markers which are identified with monoclonol antibodies.

*Cancer Research* 47:1634–1645, 1987, describes the use of x-ray lethally-irradiated human fibroblast cell mats to isolate and to culture putative human fetal kidney epithelial stem cells which are deficient in gap junctional intercellular communication. The medium used was a modified Eagle's minimum essential medium with increased amount of amino acids and vitamins, and supplemented with sodium pyruvate and fetal bovine serum.

It is an object of the present invention to describe a substantially purified human breast epithelial cell type which has stem cell characteristics.

It is another object of the present invention to describe a technique to obtain human breast epithelial cells, from reduction mammoplasty, that have stem cell characteristics by using a serum-free defined medium (the MSU-1 medium as defined below) to grow two types of normal human breast epithelial cells (HBEC) (i.e., Type I cells with stem cell and luminal epithelial cell characteristics and Type II cells with basal epithelial cell characteristics) and by separating these two types of cells into substantially pure cultures using two contrasting characters: 1) growth promotion and growth inhibition of Type I and Type II HBEC, respectively, by fetal bovine serum, and 2) late and early attachment on plastic culture dishes of Type I and Type II HBEC, respectively, after trypsinization and subculture.

It is yet another object of the present invention to describe a defined culture medium (the MSU-1 medium) that is comprised of a 1:1 (v/v) mixture of a modified Eagle's MEM and a modified MCDB 153, supplemented with recombinant human epidermal growth factor, insulin, hydrocortisone, human transferrin, 3,3',5-D.L.-triiodo thyronine and 17-β estradiol. The medium supports the growth of both Type I and Type II HBEC.

These and other objects will be described hereinafter.

SUMMARY OF THE INVENTION

Described is a substantially purified human breast epithelial cell (Type I HBEC), derived from reduction mammoplasty, comprised of the following characteristics:
  cell morphology: variable in shape;
  colony morphology: boundary smooth;
  gap junctional intercellular communication: deficient;
  fetal bovine serum: growth promotion;
  cholera toxin: inducing conversion of Type I HBEC to Type II HBEC; and
  when subjected to growth in the MSU-1 medium supplemented with fetal bovine serum, the cell has the following expression of:
  epithelial membrane antigen: positive;
  keratin 18: positive;
  keratin 14: negative;
  α6 integrin: negative
  gap junction genes (Cx26, Cx32, Cx43): negative.

When transfected by SV40, the Type I HBEC acquired the ability to grow in soft agar (anchorage independent growth, AIG$^+$) in contrast to Type II HBEC and those HBEC reported in literature (which are AIG$^-$). These SV40 transformed Type I HBEC exhibit extended lifespan and a greater tendency to become immortal and neoplastically transformed. Furthermore, the in vitro transformed Type I HBEC and breast carcinoma cell lines (e.g., MCF-7 and T47D) displayed a phenotype similar to that of Type I HBEC rather than those of our Type II HBEC and HBEC commercially available (Clonetics).

This last feature described in the above-paragraph and the ability of Type I HBEC to be induced by cholera toxin to differentiate into Type II HBEC in addition to their greater proliferation potential indicate that Type I HBEC have stem cell characteristics.

Also described is a method of obtaining the above identified epithelial cell comprising the steps of:
  a) development of a mixture of human breast epithelial cells from reduction mammoplasty tissues using the MSU-1 medium;
  b) eliminating stromal fibroblasts by a trypsin (0.002%) and ethylenediamine tetraacetic acid (EDTA) (0.02%) solution;
  c) separating Type I HBEC (with stem cell and luminal epithelial cell characteristics) from Type II HBEC (with basal epithelial cell characteristics) by collecting Type I HBEC that remain in suspension and do not attach on plastic surface for 1–2 days after trypsinization and incubation; and
  d) the continued culture of these cells in MSU-1 medium supplemented with fetal bovine serum gives rise to Type I HBEC with stem cell and luminal epithelial cell characteristics.

Described also is a substantially purified epithelial stem cell having the characteristics of the epithelial cell described above.

Also described is a method of obtaining the epithelial stem cell utilizing the steps for obtaining the substantially purified epithelial cell.

Described also is a new defined medium (the MSU-1 medium) that supports the growth of two types of normal human breast epithelial cells (Type I and Type II HBEC).

BRIEF DESCRIPTION OF THE DRAWINGS

FIGS. 5A–5D are photograph showing immunofluorescence staining of the cells of the present invention (A,B) compared to the prior art (C,D) for the expression of α6 and β4 integrins, the present invention is negative in α6 integrin expression in contrast to the prior art;

FIGS. 6A–6D show immunofluorescence staining of Simian Virus 40 (SV40) transfected with cells of the present invention (B) and cells of the prior art (D) as contrasted with non-transfected cells of the present invention (A) and those of the prior art (no staining shown) (C), for the expression of SV40 large T-antigen, the SV40 transfected cells are positive in large T-antigen expression.

DESCRIPTION OF PREFERRED EMBODIMENTS

Figure 1A:
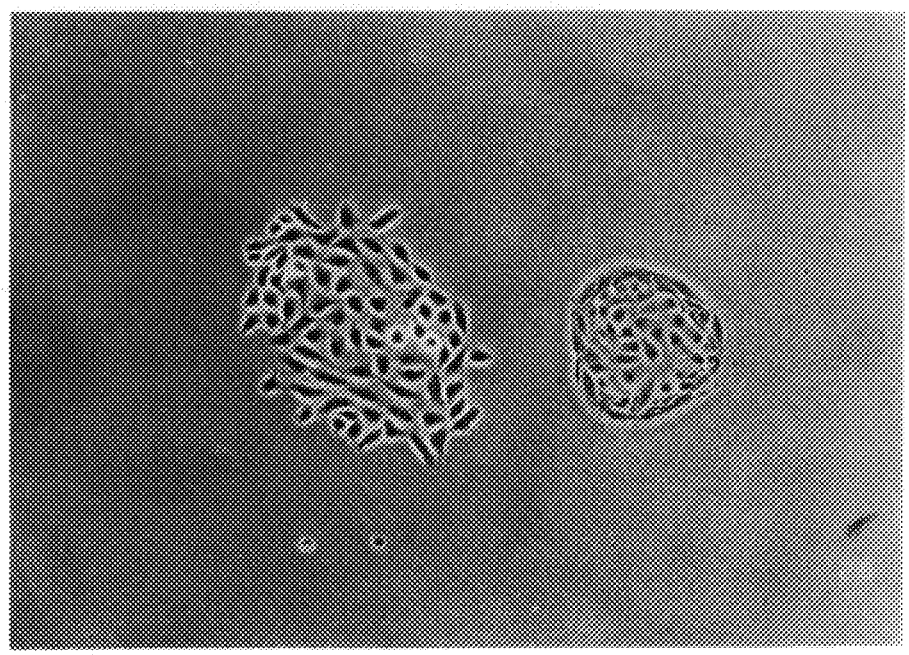
FIGS. 1A–1B are photograph of the first passage of the cells of the present invention (A-right and B) and the prior art (A-left)

A culture method to grow two morphologically distinguishable normal human breast epithelial cell types derived from reduction mammoplasty has been developed. Type I cells (present invention) are characterized by a more variable cell shape, smooth cell colony boundaries, the expression of epithelial membrane antigen (EMA), keratin 18 and the non-expression of keratin 14 and α6 integrin, and gap junction genes for Cx26, Cx32, and Cx43. In addition, the Type I cells (present invention) were growth stimulated by fetal bovine serum (FBS) and were deficient in gap junctional intercellular communication (GJIC). In contrast, Type II cells (prior art) were characterized by a uniform cell shape, expression of keratin 14, α6 integrin and the non-expression of EMA and keratin 18. In addition, Type II cells (prior art) were growth inhibited by FBS and were proficient in GJIC. Type I cells can be induced by cholera toxin to change their morphology to a Type II cell morphology. Hence Type I cells antigenically resemble luminal epithelial cells while the Type II cells more closely resemble basal epithelial cells. Type I and Type II cells were transfected with SV40 DNA. Clones with extended life were obtained from both Type I. and Type II cells by SV40 transfection. Some (2/9) of the SV40 transfected Type I cell clones became immortal (>100 cumulative population doubling level), whereas none (0/8) of the SV40 transfected Type II cell clones became immortal. The SV40 transfected Type I and Type II cell-derived extended life clones and immortal cell lines phenotypically resembled their parental cells with respect to EMA, keratin 14 and keratin 18 expression and GJIC. Each (9/9) of the SV40 transfected Type I cell clones grew in soft agar; none (0/8) of the SV40 transfected Type II cell clones were capable of growing in soft agar. These results provide evidence that normal human breast epithelial cells, derived from reduction mammoplasty, can be separated into two morphologically and antigenically different cell types and that these two different cell types significantly differ in their response to an oncogenic (SV40) stimulus. The ability of Type I HBEC to differentiate into Type II HBEC, the demonstration of Type I HBEC as target cells for neo-plastic transformation (according to stem cell theory of carcinogenesis) in addition to high proliferation potential of these cells indicate that Type I HBEC (the present invention) have stem cell characteristics.

The subject stem cell compositions may find use in a variety of ways. Since the cells are primitive and undifferentiated, they can be used to fully reconstitute an irradiated host and/or a host subject to chemotherapy; or used as a source of cells for specific lineages, by providing for their maturation, proliferation and differentiation into one or more selected lineages by employing a variety of factors, such as erythropoietin, colony stimulating factors, e.g., GM-CSF, G-CSF, or M-CSF, interleukins, e.g., IL-1, -2, -3, -4, -5, -6, -7, -8, etc., or the like, or stromal cells associated with the stem cells.

The stem cells may also be used in the isolation and evaluation of factors associated with the differentiation and maturation of hematopoietic cells. Thus, the stem cells may be used in assays to determine the activity of media, such as conditioned media, evaluate fluids for cell growth activity, involvement with dedication of particular lineages, or the like.

The stem cells may be used for the treatment of genetic diseases. Genetic diseases associated with hematopoietic cells may be treated by genetic modification of autologous or allogeneic stem cells to correct the genetic defect. For example, diseases such as B-thalas-semia, sickel cell anemia, adenosine deaminase deficiency, recombinase deficiency, recombinase regulatory gene deficiency, etc. may be corrected by introduction of a wild-type gene into the stem cells, either by homologous or random recombination. Other indications of gene therapy are introduction of drug resistance genes to enable normal stem cells to have an advantage and be subject to selective pressure, e.g. the multiple drug resistance gene (MDR). Diseases other than those associated with hematopoietic cells may also be treated, where the disease is related to the lack of a particular secreted product such as a hormone, enzyme, interferon, factor, or the like. By employing an appropriate regulatory initiation region, inducible production of the deficient protein may be achieved, so that production of the protein will parallel natural production, even though production will be in a different cell type from the cell type that normally produces such protein. It is also possible to insert a ribozyme, antisense or other message to inhibit particular gene products or susceptibility to diseases, particularly hematolympho-tropic diseases.

The epithelial cells of the Type I that are obtained herein are stem cell in nature. Stem cells have utility for skin grafting techniques as well as for liver regeneration. They have utility for treating those that are suffering from anemia, Hodgkin's disease, or juvenile leukemia.

Being able to obtain the putative human breast epithelial stem cells of the present invention enables one to further perform research on carcinogenesis to develop chemopreventive and therapeutic strategies for breast cancer.

CULTURE MEDIA
Type I HBEC (present invention): MSU-1 medium or MSU-1 with 5% fetal bovine serum;
Type II HBEC (prior art): MSU-1 medium or MSU-1 with 0.4% bovine pituitary extract and cholera toxin (1 ng/ml)

| Components of MSU-1 Medium | mg/Liter |
| --- | --- |
| Ammonium Metavanadate ($NH_4VO_3$) | 0.000293 |
| Calcium Chloride.$2H_2O$ ($CaCl_2.2H_2O$) | 143.5 |
| Cupric Sulfate.$5H_2O$ ($CuSO_4.5H_2O$) | 0.00138 |
| Ferrous Sulfate.$7H_2O$ ($FeSO_4.7H_2O$) | 0.695 |
| Magnesium Chloride.$6H_2O$ ($MgCl_2.6H_2O$) | 61 |
| Magnesium Sulfate (anhydrous) ($MgSO_4$) | 48.84 |
| Magnesium Sulfate ($MnSO_4$) | 0.0000755 |
| Molybdic Acid.$4H_2O$ (ammonium) | 0.000618 |

CULTURE MEDIA

Type I HBEC (present invention): MSU-1 medium or MSU-1 with 5% fetal bovine serum;
Type II HBEC (prior art): MSU-1 medium or MSU-1 with 0.4% bovine pituitary extract and cholera toxin (1 ng/ml)

| Components of MSU-1 Medium | mg/Liter |
|---|---|
| [$(NH_4)_6Mo_7O_{24}.4H_2O$] | |
| Nickel Chloride.$6H_2O$ ($NiCl_2.6H_2O$) | 0.0000594 |
| Potassium Chloride (KCl) | 127.96 |
| Sodium Bicarbonate ($NaHCO_3$) | 1088 |
| Sodium Chloride (NaCl) | 7617 |
| Sodium Metasilicate.$9H_2O$ ($Na_2SiO_3.9H_2O$) | 0.071 |
| Sodium Phosphate Dibasic (anhydrous) ($Na_2HPO_4$) | 142.04 |
| Sodium Phosphate Monobasic (anhydrous) ($NaH_2PO_4$) | 61 |
| Sodium Selenite ($Na_2SeO_3$) | 0.00193 |
| Stannous Chloride.$2H_2O$ ($SnCl_2.2H_2O$) | 0.0000565 |
| Zinc Sulfate.$7H_2O$ ($ZnSO_4.7H_2O$) | 0.0719 |
| L-Alanine | 13.36 |
| L-Arginine.HCl | 199.85 |
| L-Asparagine.$H_2O$ | 22.5 |
| L-Aspartic Acid | 15.3 |
| L-Cysteine.HCl.$H_2O$ | 21 |
| L-Cystine.2HCl | 23.5 |
| L-Glutamic Acid | 22 |
| L-Glutamine | 584.6 |
| Glycine | 11.26 |
| L-Histidine.HCl.$H_2O$ | 65.04 |
| L-Isoleucine | 89.19 |
| L-Leucine | 71.8 |
| L-Lysine.HCl | 63.64 |
| L-Methionine | 20.21 |
| L-Phenylalanine | 33.92 |
| L-Proline | 28.77 |
| L-Serine | 42 |
| L-Threonine | 42 |
| L-Tryptophan | 13.62 |
| L-Tyrosine.2Na | 49.23 |
| L-Valine | 52.06 |
| D-Biotin | 0.0073 |
| Choline Chloride | 7.73 |
| Folic Acid | 1.15 |
| myo-Inositol | 10.51 |
| Niacinamide | 0.768 |
| D-Pantothenic Acid (hemicalcium) | 0.869 |
| Pyridoxine.HCl | 0.781 |
| Riboflavin | 0.094 |
| Thiamine.HCl | 0.919 |
| DL-6,8-Thioctic Acid | 0.103 |
| Vitamin B-12 | 0.204 |
| Adenine.HCl | 15.44 |
| Ethanolamine | 4.88 |
| D-Glucose | 1040 |
| HEPES | 3300 |
| Phenol Red.Na | 0.621 |
| Phosphoethanolamine | 7.06 |
| Putrescine.2HCl | 0.081 |
| Pyruvic Acid.Na | 82.5 |
| Sodium Acetate (anhydrous) | 150.77 |
| Thymidine | 0.364 |
| Human Recombinant Epidermal Growth Factor | 0.0005 |
| Human Transferrin | 5 |
| Hydrocortisone | 0.5 |
| Insulin | 5 |
| 17-β estradiol | 0.002724 |
| 3,3',5-triiodo-DL-thyronine | 0.01302 |

It is to be appreciated that some components of the aforementioned medium are essential and some components of the medium are not essential for cell growth and that the optimum range of amount of each component may vary greatly. Therefore, the kind and amount of the components may be modified without departing from the scope of the invention.

Materials And Methods

Culture Media. The medium used in these studies, identified as "MSU-1" medium, is a 1:1 mixture (v/v) of a modified Eagle's MEM (GIBCO BRL Life Technologies, Inc., Grand Island, N.Y.) and a modified MCDB 153 (Sigma Chemical Co., St. Louis, Mo.) supplemented with human recombinant epidermal growth factor (0.5 ng/ml) (E-1264, Sigma), insulin (5 ug/ml) (I-1882, Sigma), hydrocortisone (0.5 ug/ml) (H-0888, Sigma), human transferrin (5 ug/ml) (T-7786, Sigma), 3,3',5-triiodo-D.L.-thyronine ($2\times10^{-8}M$) (T-2627, Sigma), and 17 β-estradiol ($1\times10^{-8}M$) (E-2257, Sigma). The modified Eagle's MEM (7) contains Earle's balanced salt solution with 1 mg/ml sodium bicarbonate and 7.64 mg/ml sodium chloride, a 50% increase in all vitamins and essential amino acids (except glutamine), and a 100% increase in all nonessential amino acids and 1 mM sodium pyruvate (pH adjusted to 6.5 before the addition of sodium bicarbonate). The modified MCDB 153 was prepared from commercial MCDB 153 (8) powdered medium (M-7403, Sigma), supplemented with 0.1 mM ethanolamine (E-6133, Sigma), 0.1 mM phosphoethanolamine (P-0503, Sigma), $1.5\times10^{-4}M$ calcium and amino acids, i.e. isoleucine ($7.5\times10^{-4}M$), histidine ($2.4\times10^{-4}M$), methionine ($9\times10^{-5}M$), phenylalanine ($9\times10^{-5}M$), tryptophan ($4.5\times10^{-5}M$) and tyrosine ($7.5\times10^{-5}M$) (9) (Sigma). The pH of this medium was also adjusted to 6.5 before the addition of sodium bicarbonate ($1.4\times10^{-2}M$).

Acquisition Processing and Culturing of Human Breast Epithelial Cells (HBEC). All reduction mammoplasty tissues were obtained from female patients of 21–29 years of age. A total of 7 reduction mammoplasty tissue specimens, from 7 different patients, were examined in these studies. The HBEC that were obtained from the 7 reduction mammoplasty tissue specimens were designated HME-5, 6, 8, 11, 12, 13 and 14. The tissue specimens were minced into small pieces with scalpels, then digested in collagenase-Type IA (C-9891, Sigma) solution (1 g tissue / 10 mg of collagenase in 10 ml medium) at 37° C. in a waterbath overnight (16–18 hr). The next morning, the solution containing the digested tissues was centrifuged to remove the collagenase solution. The cellular pellet was washed once with MSU-1 medium before being suspended in the MSU-1 medium supplemented with 5% fetal bovine serum (FBS) (GIBCO). Subsequently, the cells were plated in two flasks (150 $cm^2$). After a 2 hour incubation, the cells (or cell aggregates) which remained in suspension were transferred to 4–6 flasks (75 $cm^2$) for the purpose of reducing the number of attached fibroblasts. After an overnight incubation, the medium was changed to the FBS-free MSU-1 medium. The MSU-1 medium was changed once every 2 days for 1 week. Subsequently, the cells were removed with solutions of trypsin (0.01%) (Sigma) and ethylenediamine tetraacetic acid (EDTA) (0.02%) (Sigma) and stored in solution [phosphate buffered saline (PBS) containing 10% dimethyl sulfoxide] in liquid nitrogen. During this week period, virtually all of the fibroblasts can be removed by treatment (1–2 times) with diluted trypsin (0.002%) and EDTA (0.02%) solution.

To start a culture from stored frozen cells in liquid nitrogen, the cells were thawed and placed in the MSU-1 medium supplemented with 5% FBS for 4 hours for the attachment of residual fibroblasts. The epithelial cells in suspension were transferred to new flasks and cultured in the FBS-free MSU-1 medium. All cultures were incubated at 37° C. in incubators supplied with humidified air and 5% $CO_2$.

Separation of the Two Types of HBEC. The first passage of HBEC, recovered from liquid nitrogen storage, was plated in MSU-1 medium supplemented with 5% FBS. After overnight culture, the cells which remained in suspension, were transferred to new plates. Continued culture of these cells in the FBS-containing medium gave rise to one morphological type of cell. The attached cells, in the overnight culture, cultured in the FBS-free MSU-1 medium supplemented with cholera toxin (1 ng/ml) (Sigma) and 0.4% bovine pituitary extract (Pel-Freez, Rogers, AR) gave rise to a second morphological type of cell. The rare contaminants of the other cell type in these cultures were removed by mechanically scraping the unwanted small colonies once they were morphologically recognizable.

Assessment of the Characteristics of Cultured HBEC

1. Morphology. The normal HBEC with the two different types of morphology can be observed and easily distinguished under a Nikon phase contrast microscope without any treatment.

2. Immunocytochemical Analysis. HBEC, grown on 35 mm culture dishes for colony development or until 50% confluent, were rinsed with PBS and fixed with formaldehyde (3.7% in PBS) for 10 minutes. After treatment with 95% ethanol for 5 minutes, the cells were incubated with bovine serum albumin (BSA) (1% in PBS) for 30 minutes. This was followed by treatment with the primary antibody against the target molecules (prepared in PBS containing 0.1% BSA) for 30 minutes. The cells were then incubated with biotin-conjugated bridging antibody (Sigma) and then with fluorescein isothiocyanate (FITC)-conjugated streptavidin (Sigma) (in PBS with 0.1% BSA) for 30 minutes. All treatments were carried out at room temperature. Following each treatment, the cells were thoroughly rinsed with PBS (5–6 times). The monoclonal antibodies against keratin 14 (C-8791) and keratin 18 (C-8541) were obtained from Sigma. The monoclonal antibody against EMA was a gift from Dr. M. G. Ormerod of the Institute of Cancer Research, Royal Cancer Hospital (Sutton, Surrey, UK) (38). The monoclonal antibodies to integrin $\alpha 6$ (BQ16) and $\beta 4$ (UM-A9) (10) were gifts from Dr. M. Liebert of the University of Michigan, Ann Arbor, Mich. Cells for integrin immunostaining were treated differently than those for keratin 14, 18 and EMA. These cells were fixed with paraformaldehyde (4% in PBS) for 30 minutes. Subsequently, the cells were placed in ice-cold methanol for 30 seconds. After permeablization, the cells were washed with PBS and incubated in a 3% BSA and 0.1% Tween 20 solution for 1.5 hr to block non-specific binding. Subsequently, the cells were incubated with the primary antibodies against integrin $\alpha 6$ and $\beta 4$ for 1.5 hr at room temperature. Without using the bridging antibody, the primary antibody-treated cells were incubated for 1.5 hr in the dark with FITC-conjugated goat anti-mouse IgG (Jackson ImmunoResearch Lab., Inc. West Grove, Pa.) (in PBS containing 1% BSA and 0.01% Tween 20). The fluorescence was detected and analyzed by a ACAS 570 cell analyzer (Meridian Instruments, Okemos, Mich.).

Although antibodies to EMA and $\alpha 6/\beta 4$ integrins were obtained from private sources for this study, they are also commercially available (e.g., EMA: Vector Laboratories, NCL-EMA, Zymed Laboratories, Inc., 18-0017; $\alpha 6/\beta 4$ integrins: Chemicon International, Inc. MAB1973, AB 1922).

3. Gap Junctional Intercellular Communication (GJIC). GJIC was studied by the scrape loading/dy transfer technique previously developed in this laboratory (11). HBEC were grown to 80% confluency in 35 mm culture dishes, rinsed several times with PBS, and exposed to 0.05% Lucifer yellow (Sigma) dye solution in PBS. Several cuts were made on the monolayer of cells with a scalpel in the presence of the dye mixture to load the dye into cells. The cells remained in the dye solution at room temperature for four minutes. After removing the dye solution, the cells were rinsed several times with PBS and examined using Nikon, a phase contrast epifluorescence microscope to assess the extent of dye transfer.

Treatment of Cultured HBEC with SV40 DNA

SV40 viral DNA was purchased from GIBCO BRL Life Technologies. The transfection was mediated by lipofectin (GIBCO). The two cellular types of HBEC were plated on 60 or 90 mm plates. When the cells reached 50~70% confluency (each plate contained approximately $2-3\times10^6$ cells), they were washed with the FBS-free MSU-1 medium twice, then incubated with 3 ml of FBS-free MSU-1 medium containing SV40 DNA (0.67 ug/ml) and lipofectin (10 ug/ml) at 37° C. for hours. The next day, the lipofectin containing medium was replaced with the MSU-1 medium (with or without FBS, for the two different types of HBEC) and the cells were cultured for 3 days. The SV40 treated cells were subcultured and replated in 9 cm plates at a lower cell density to provide more room for cell growth and colony formation. The cells which were able to form large colonies could be easily distinguished from the non-transfected cells which senesced after subculture. Developing colonies from the two cellular types of HBEC after SV40 transfection were isolated by the trypsin/glass ring method for further characterization. HBEC from three reduction mammoplasty specimens (from 3 different patients, i.e. HME-11, HME-13, and HME-14) were used for the SV40 transfection. The expression of SV40 large T-antigen in the SV40 transfected HBEC was examined by immunostaining using the monoclonal antibody AB-2 (Oncogene Science, Inc., Uniondale, N.Y.). The immunostaining procedure for SV40 large T-antigen is similar to the method used for the keratin 14, 18 and EMA antibodies described previously.

Anchorage Independent Growth (AIG). 0.5% Agarose (Type I, low electroendosmosis (EEO) Sigma), prepared in MSU-1 medium at 39° C. was added to 60 mm culture dishes and allowed to solidify in the incubator. HBEC cells ($2\times10^4$), suspended in the medium at 39° C. with 0.33% agarose, were overlaid on top of the hard agar layer. Plates were incubated at 37° C. and liquid medium was added 3 days after HBEC inoculation and renewed every 3 days. After 3~4 weeks of incubation, the AIG colonies were observed between the two agarose layers and the size of the colony was determined.

Assessment of Cell Proliferation Potential. The cumulative population doubling level (cpdl) was determined by calculating the initial (Ni) and final (Nf) HBEC number using the formula: pdl=ln (Nf/Ni)/ln 2, where in is the natural log. SV40 transfected HBEC, which exhibited higher proliferative activities than non-SV40 transfected HBEC, are referred to as having extended life (EL). SV40 transfected HBEC which were propagated continuously (a cpdl of 100 or greater) are referred to as being normal.

Results

Characteristics of HBEC in Culture

Morphology of the Two Types of HBEC. Single HBEC or HBEC aggregates from reduction mammoplasty tissues began to proliferate in MSU-1 medium within 2 days. These initial cell cultures were subcultured and stored in liquid nitrogen at day 7. The first passage cells, subcultured from the initial culture or thawed from the preserved cells in liquid nitrogen, when cultured in the FBS-free MSU-1 medium, formed two morphologically distinguishable colonies (FIG. 1A). The first colony type contained cells that were elongated and variable in shape, less reflective and less distinctive in cell boundary (FIG. 1A-right and 1B). The cells in this colony are herein referred to as Type I cells. The second colony type, herein referred to as Type II, contained cells that were more uniform in cell shape (cobble stone-shaped) and have a conspicuous cell boundary (FIG. 1A-left). The edge of Type I cell colonies is smooth and appears to be bounded by a layer of elongated cells in contrast to the non-constrained outline of Type II cell colonies. The presence of these two types of colonies/cells has been consistently observed in all seven HBEC primary cultures examined, i.e. HME-5, 6, 8, 11, 12, 13 and 14. The frequencies of these two types of colonies/cells vary among the seven different HBEC cultures, e.g. the frequencies of Type I/Type II colonies at early passage for HME-5, HME-6, and HME-8 are 45%/55%, 9%/91% and 72%/28%, respectively. In addition to Type I and Type II cell colonies, some colonies containing both Type I and Type II cells were also observed (FIG. 2B and C-left). In these colonies, Type I cells were invariably situated at the center of the colony and were completely or partially surrounded by Type II cells. This spontaneously morphological change of Type I cells into Type II cells has been observed in each of the 7 HBEC cultures.

Development of Enriched Type I HBEC Cultures. One major different between Type I and Type II cells is their growth response to FBS. Type I cells are stimu- lated to grow by FBS whereas Type II cells are growth inhibited by FBS (29). A second difference between Type I and Type II cells is that after subculture, Type II cells attach to plastic plates earlier than do Type I cells. Many Type I cells still remain in suspension in the medium one day after trypsinization and replating. These cells can be transferred to a new plate to obtain a culture enriched in Type I cells. Adding FBS to the culture medium (inhibits the growth of Type II cells) can further enrich the cultures for Type I cells.

Induction By Cholera Toxin of Type I HBEC Into Type II HBEC. The first passaged HBEC (HME-5 and 8) were inoculated in MSU-1 medium in the presence or absence of cholera toxin (1 ng/ml). After 10–12 days, the frequencies of three types of colonies (Type I cells only, Type II cells only and both Type I and Type II cells) were determined. The results from these experiments consistently showed that cholera toxin significantly (P<0.01) increased the frequency of colonies containing both types of cells (Table 1). The frequency of colonies exemplified by Type I cells sur- rounded by Type II cells, in the presence of cholera toxin, was increased from 28% to 43%, 11% to 16% and 3% to 9%, respectively. The total number of colonies was not significantly influenced by cholera toxin. In the second experiment, HBEC (HME-14) enriched for Type I cells were inoculated in MSU-1 medium in the presence or absence of cholera toxin (1 ng/ml). After 10 days, in the presence of cholera toxin, the frequency of colonies with Type II cells was found to be significantly (P<0.01) increased (from 10% to 18%), while the total number of colonies was not significantly changed (Table 1). These results provide evidence that treatment with cholera toxin enhances the transition of Type I cells into Type II cells.

TABLE 1

Effect Of Cholera Toxin On Frequencies of Type I, Type II and Type 1/Type II Colonies Developed From Early Passage HBEC

| HBEC | Cholera Toxin (1 ng/ml) | Total Colonies (No. of Plate) | Type I Cells Only | Colony Type - Type I Cells Surrounded By Type II Cells | Type II Cells Only |
|---|---|---|---|---|---|
| HME-5[a] | − | 301 (4) | 95 (31%) | 83 (28%) | 123 (41%) |
|  | + | 362 (4) | 44 (12%) | 155 (43%) | 163 (45%) |
| HME-8[a] | − | 1477 (4) | 940 (64%) | 161 (11%) | 376 (25%) |
|  | + | 1941 (4) | 1147 (59%) | 315 (16%) | 479 (25%) |
| HME-8[a] |  | 1918 (10) | 1421 (74%) | 54 (3%) | 443 (23%) |
|  |  | 1716 (10) | 1249 (73%) | 150 (9%) | 317 (18%) |
| HME-14[b] | − | 723 (3) | 652 (90%) |  | 71 (10%) |
|  | + | 666 (3) | 547 (82%) |  | 119 (18%)[c] |

[a]Early passage HBEC (HME-5 and 8) were inoculated in MSU-1 medium supplemented with 5% FBS for 1 day. The medium was changed to MSU-1 with or without cholera toxin the next day, and the cells were incubated for a total of 10 days for colony development. The colony-forming efficiencies were 15% and 18% in the absence and presence of cholera toxin, respectively for HME-5.
[b]HBEC (HME-14) enriched for Type I cells were inoculated in MSU-1 medium supplemented with 5% FBS for 1 day. The medium was changed to MSU-1 with or without cholera toxin the next day, and the cells were incubated for a total of 10 days for colony development.
[c]The frequencies of Type 1/Type II cell colonies (HME-5 and 8) or Type II cell colonies (HME-14) are significantly higher upon cholera toxin treatment (P < 0.01) (12).

Figure 3A:
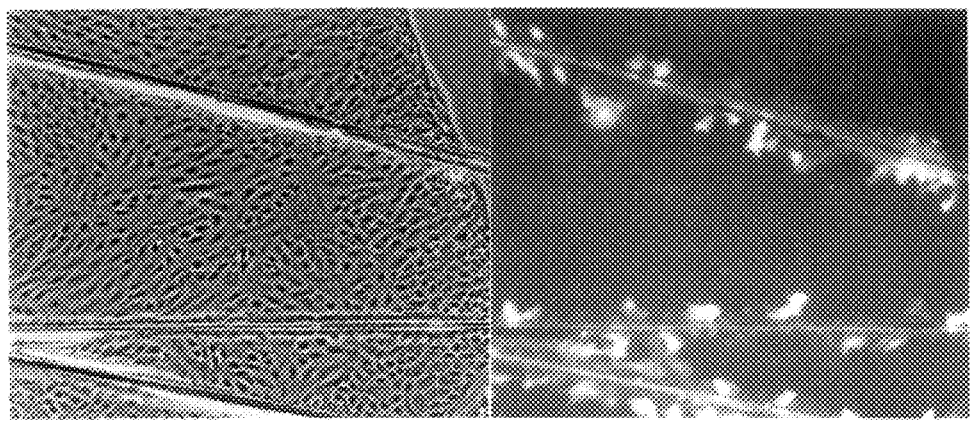
FIGS. 3A–3B are photograph showing the deficiency of gap junctional intercellular communication (GJIC) for the cells of the present invention (A), while the prior art cells (B) are shown to be competent in GJIC.
Figure 3B:
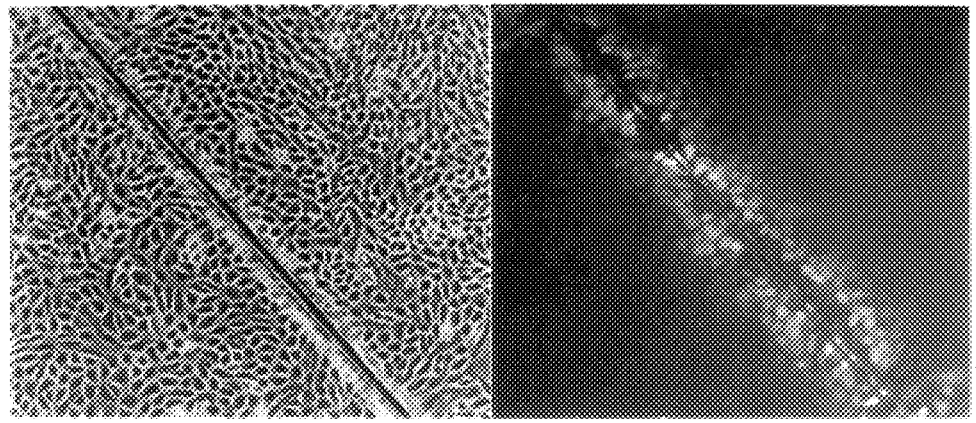

GJIC in Type I and Type II HBEC. Type I cells and Type II cells were examined for their ability to perform GJIC using the scrape loading/dye transfer technique. The results show that Type I cells were deficient in GJIC (FIG. 3A), while Type Ii cells were efficient in GJIC (FIG. 3B). This difference in GJIC in Type I and Type II cells was observed in each of the 7 HBEC (HME-5, 6, 8, 11, 12, 13 and 14) and was observed in both early and late passaged cells.

Figure 4:
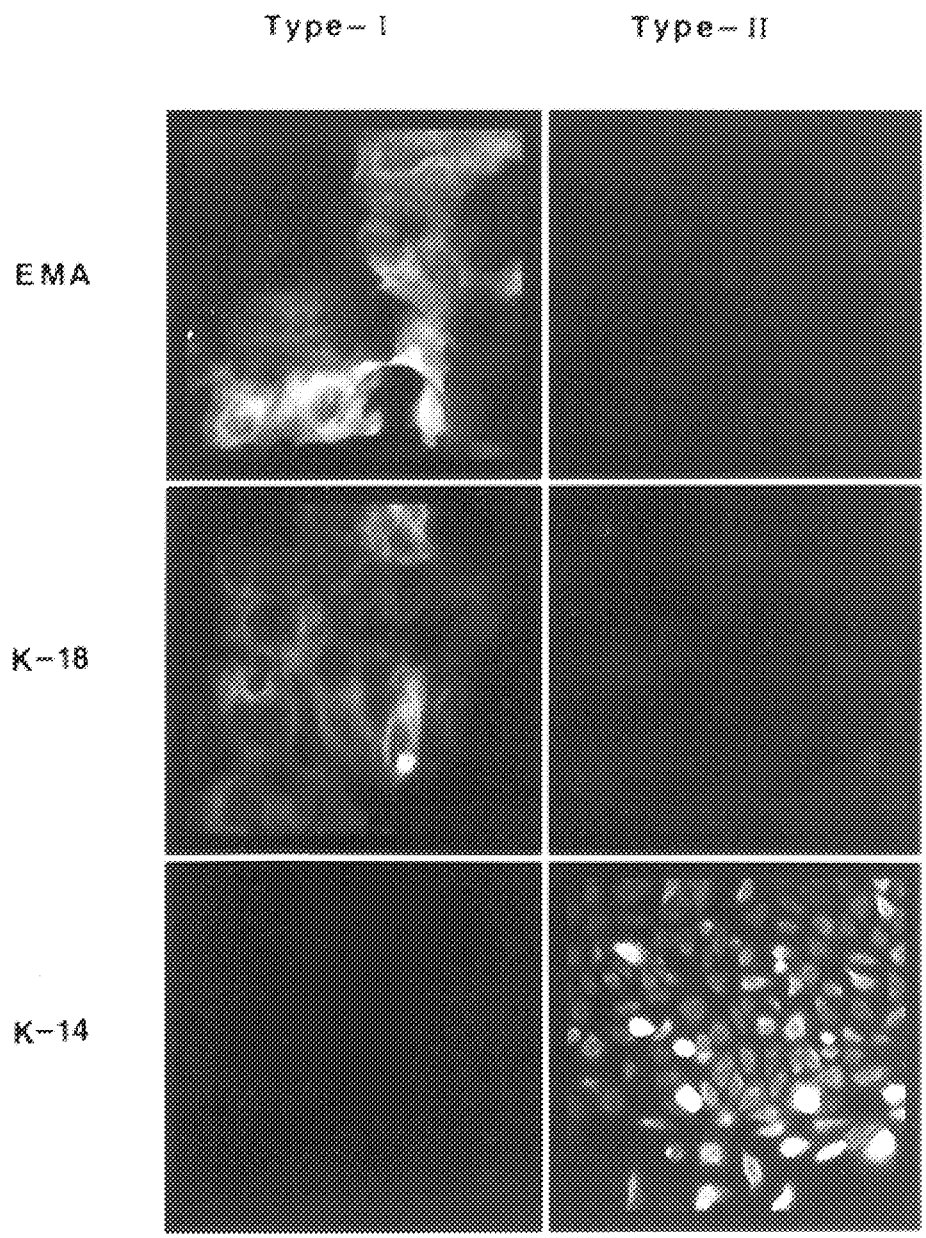
FIG. 4 is a photograph of immunofluorescence staining of the cells of the present invention (left) as compared with the prior art (right) for the expression of epithelial membrane antigen (EMA) (top), keratin 18 (middle), and keratin 14 (bottom), the positive expression of EMA and keratin 18 and negative expression of keratin 14 are shown for the present invention.

Expression of EMA, Keratins 14 and 18 and $\alpha b/\beta 4$ Integrins in Type I and Type II HBEC. Three HBEC (HME-5, 11 and 12) were examined for their antigenic marker expression. The results showed that Type I cells consistently expressed EMA and keratin 18 (luminal epithelial cell markers) but not keratin 14 (basal epithelial cell marker), while Type II cells consistently expressed keratin 14 but not EMA and keratin 18 (FIG. 4). Type I cells did not express $\alpha 6$ (basal epithelial cell marker) or $\beta 4$ integrins (FIG. 5A and B) whereas Type II cells consistently expressed $\alpha 6$ integrins (FIG. 5C) but did not express $\beta 4$ integrins (FIG. 5D). That Type I and Type II cells are distinctly different in their antigenic expression has been demonstrated in these studies. A summary of the differences between Type I and Type II cells is provided in Table II.

TABLE II

Summary of Differences Between Type I and Type II HBEC

| | Type I | Type II |
|---|---|---|
| Cell morphology | Variable in shape | Uniform in shape, cobble-stone appearance |
| Colony morphology | Boundary smooth | Boundary not smooth |
| Attachment on plastic surface after trypsinization | Late | Early |
| Effect of fetal bovine serum | Growth promotion | Growth inhibition |
| Effect of cholera toxin | Induces Type I cells to change into Type II cell morphology | |
| Gap junctional intercellular communication | Deficient | Efficient |
| Expression of: | | |
| Epithelial Membrane Antigen | + | − |
| Keratin 18 | + | − |
| Keratin 14 | − | + |
| α6 Integrin | − | + |

Effect of Transfection of Type I and Type II HBEC with SV40 DNA

Isolation of SV40 Transfected HBEC Clones. Type I and Type II cells, from 3 HBEC (HME-11, 13 and 14) were transfected with SV40 DNA. After SV40 transfection, the majority of the cells became senescent and stopped proliferating within a week. Against the background of senescent cells, a few colonies containing proliferating cells became evident. These colonies (clones) were isolated for continual growth expansion and further characterization. A total of 9 independent Type I cell-derived SV40 transfected colonies were isolated from HME-11 (referred to as M11SV-1, 2, 3, 4 and 5), HME-13 (referred to as M13SV-1 and 2) and HME-14 (referred to as M14SV-1 and 2). A total of eight independent Type II cell-derived SV40 transfected colonies were isolated from HME-11 (referred to as M11SV-21 AND 22), HME-13 (referred to as M13SV-21, 22 and 23) and HME-14 (referred to as M14SV-21, 22 and 23). Immunocytochemical analysis, using antibodies against SV40 large T-antigen, showed that each of the isolated clones were positive for the expression of SV40 large T-antigen whereas the non-transfected parental cells were negative (FIG. 6, Table III). The expression of SV40 large T-antigen in the SV40 transfected Type I and Type II cells were restricted to the nuclei.

TABLE III

Summary of Characteristics of SV40 Transfected Type I and Type II HBEC

| | SV-40 T-antigen | EMA | K-18 | K-14 | GJIC | AIG |
|---|---|---|---|---|---|---|
| TYPE I | | | | | | |
| M11SV-1 | + | + | ++ | − | − | + |
| M11SV-2 | + | + | ++ | − | − | + |
| M11SV-3 | + | + | ++ | − | − | + |
| M11SV-4 | + | + | ++ | − | − | + |
| M11SV-5 | + | + | ++ | − | − | + |
| M13SV-1 | + | + | ++ | − | − | + |
| M13SV-2 | + | + | ++ | − | − | + |
| M14SV-1 | + | + | ++ | − | − | + |
| M14SV-2 | + | + | ++ | − | − | + |
| TYPE II | | | | | | |
| M11SV-21 | + | − | −(+) | + | N.D. | − |
| M11SV-22 | + | − | −(+) | + | + | − |
| M13SV-21 | + | − | − | + | N.D. | − |
| M13SV-22 | + | − | − | + | + | − |
| M13SV-23 | + | − | − | + | + | − |
| M14SV-21 | + | − | − | + | N.D. | − |
| M14SV-22 | + | − | − | + | N.D. | − |
| M14SV-23 | + | − | − | + | N.D. | − |

*abbreviations:
EMA, epithelial membrane antigen;
K-18, keratin 18;
K-14, keratin 14;
GJIC, gap junctional intercellular communication;
AIG, anchorage independent growth;
N.D., not done;
+, positive,
++, strong positive;
−, negative;
−(+), heterogeneous.

Proliferation Characteristics of SV40 Transfected Type I and Type II HBEC. The cpdl was determined for each of the clones of SV40 transfected Type I and Type II cells. Almost all of the SV40 transfected clones had an extended lifespan, a phenomenon independent as to whether or not the clones were derived from Type I or Type II cells, maximum cpdl ranging from 20~50, i.e., Type I, cpdl, mean ±S.E.= 34.4±2.7; Type II, cpdl, mean ±S.E.=27.2±2.1). Two of the clones (2/9) (M13SV-1 and M13SV-2), both derived from SV40 transfected Type I cells, became immortal (with and without crisis for M13SV-1 and M13SV-2, respectively), having a cpdl greater than 100. None of the Type II cell-derived SV40 transfected clones (0/8) became immortal.

Characterization of SV40 Transfected Type I and Type II Cells. The expression of EMA, keratin 18, keratin 14 and the ability to perform GJIC in the SV40 transfected Type I cell clones and Type II cell clones were found to mimic their parental counterparts, i.e., the expression of EMA, keratin 18 and GJIC deficiency was observed in Type I cell clones and the expression of keratin 14 and GJIC proficiency was observed in the Type II cell clones. These data are summarized in Table III.

Figure 7A:
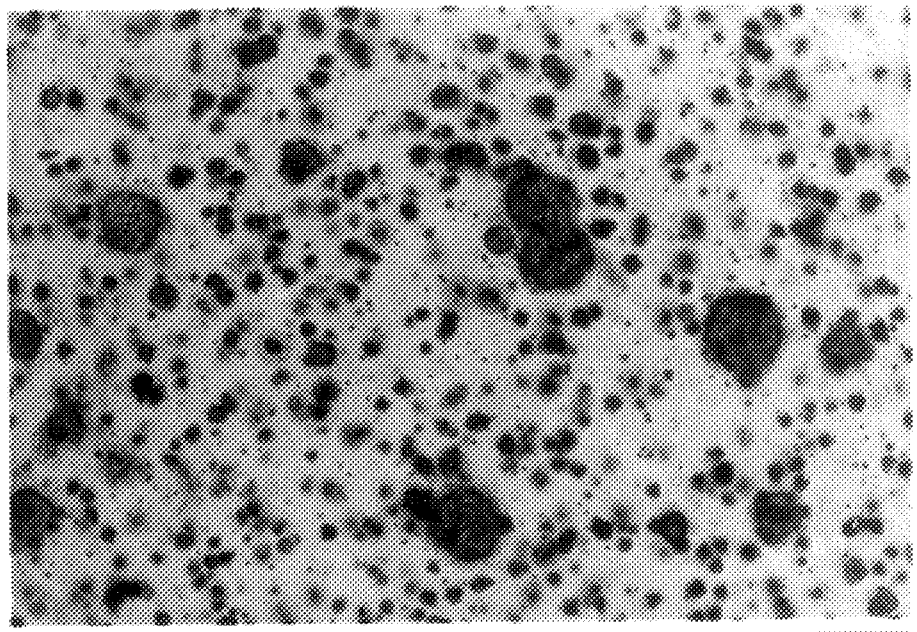
FIGS. 7A–7B are photograph of the cells of the present invention transfected by SV40 showing anchorage independent growth on the soft agar medium, the prior art did not show anchorage independent growth after SV40 transfection (data not shown).
Figure 7B:
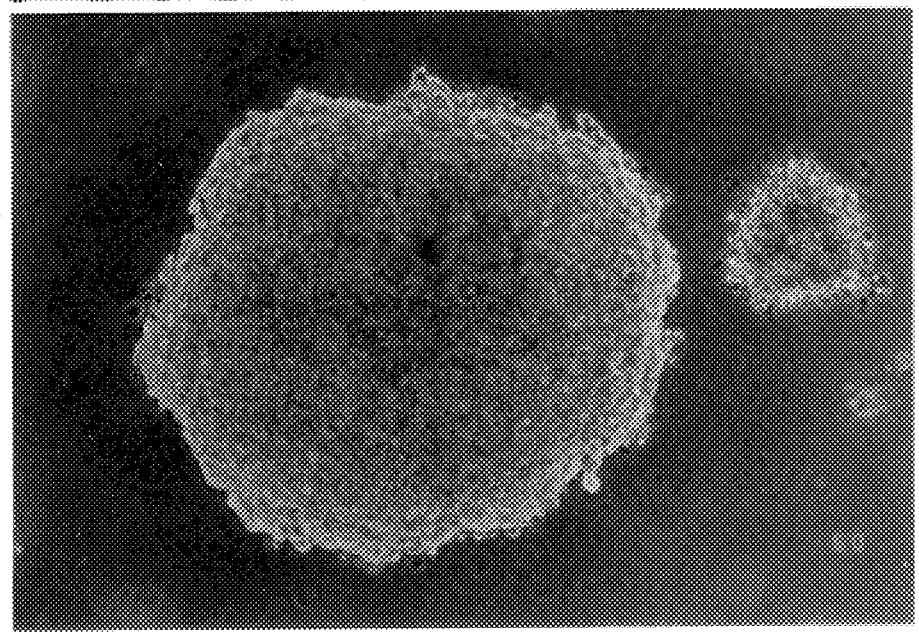

Anchorage Independent Growth (AIG) of SV40 Transfected Type I and Type II HBEC. SV40 transfected Type I and Type II cells had markedly different abilities to grow in soft agar (AIG). Each of the SV40 transfected Type I cells formed colonies in soft agar (FIG. 7, Table III). The colony-forming frequency was, mean ±S.E., 7.2±2.8%. The largest colonies observed were ranged from 0.5 mm to 1 mm in diameter. In contrast, none of the SV40 transfected Type II cells formed colonies in soft agar.

Discussion

As summarized in Table 2, Type I and Type II HBEC are quite different phenotypically. Type I cells express EMA and keratin 18 but do not express keratin 14 and α6 integrin. EMA and keratin 18 expression are markers for luminal epithelial cells (1,2). Type II cells express keratin 14 and α6 integrin but do not express EMA and keratin 18. Keratin 14 and α6 integrin expression are markers for basal epithelial cells (1,3). In previously published reports in which cultures of primary HEEC were examined, it appears that the vast majority of the cultured cells, derived from reduction mammoplasty, more closely resembled, phenotypically, Type II cells as judged by cell morphology, antigenic expression, and growth inhibition by FBS (1, 4–6).

Cultures of primary HBEC, in which the predominant phenotype is similar to Type I cells, heretofore has not been reported. Without being bound to any theory, it is believed that the reason for this may be due to the type of culture media used. The media most often used to culture primary HBEC (e.g., MCDB 170 (molecular, cellular and developmental biology), DFCI-1 (Dana-Farber Cancer Institute) (5,6) are most often supplemented with cholera toxin and/or bovine pituitary extract. These supplements favored the conversion of Type I to Type II cells. Indeed, an important observation in our studies is that one can accelerate the spontaneous change of Type I cells into Type II cells by the addition of cholera toxin to the culture medium. This not only results in a change in cellular morphology, but, in addition, results in a striking change in gene expression, e.g., the switch from EMA and keratin 18 expression to keratin 14 and $\alpha 6$ integrin expression. Furthermore, these cells become altered in their responsiveness to serum, i.e. Type I cells are growth stimulated by FBS while the growth of Type II cell is inhibited by this serum supplement. This conversion may be triggered by an increase in the cellular levels of cyclic AMP induced by cholera toxin. The culture medium disclosed herein (MSU-1) allows for the separation and/or enrichment of Type I and Type II cells upon supplementing the medium with FBS or cholera toxin/bovine pituitary extract.

The induction of immortalization of normal HBEC has been reported previously (13–22). In these studies, either HBEC derived from lactational samples (milk cells) or HBEC derived from reduction mammoplasty were utilized. Cultured milk cells most often express keratin 18 (luminal epithelial cells); on occasion, colonies of cultured milk cells will also express keratin 14 (1). Cells from reduction mammoplasty contain predominantly basal epithelial cells when cultured in MM or MCDE 170 medium (1). Utilizing the MSU-1 culture medium with or without FBS, one can enrich for these two types of cells (luminal and basal epithelial cells) and determine their differential response to a potential oncogenic stimulus.

SV40 is an oncogenic agent that has been reported by a number of laboratories to induce immortalization of primary HBEC (13, 16–22). After transfection of SV40 DNA into Type I and Type II cells, clones with extended lifespan were derived from Type I and Type II cells at comparable frequency. However, 2 of 9 of the SV40 transfected Type I cell-derived extended life clones converted to immortal cell lines, while none (0/8) of the SV40 transfected Type II cell-derived extended life clones became immortalized. Significantly, however, is the difference in anchorage independent growth (AIG) between SV40 transfected Type I and Type II cells. None (0/8) of the SV40 transfected Type II cell-derived extended life clones displayed AIG, while each (9/9) of the SV40 transfected Type I cell-derived extended life clones showed AIG. AIG is often used to identify tumor cells (23) and is frequently described as a marker for neoplastic transformation (24–26). In past reports in which SV40 was effective in the immortalization of HBEC, these immortalized cells were incapable of AIG (16–22), with the possible exception of one cell line which was selected in soft agar (13). Thus, these results demonstrate that Type I cells and Type II cells differ substantially in their response to an oncogenic stimulus (SV40), particularly with regard to AIG.

The SV40 transfected Type I and Type II cells closely resembled the phenotypes of their parental cells, such as the expression of EMA and keratins. In addition, they maintained the parental phenotype with regard to GJIC. The Type I cell-derived SV40 transfected clones also are similar in many respects to human breast carcinoma cell lines. For example, MCF-7 (Michigan Cancer Foundation, Detroit, Mich., American Type Culture Collection, HTB 22) and T47D (American Type Culture Collection, HTB 133) human breast carcinoma cell lines, which express the antigenic markers keratin 18 and EMA but not keratin 4 are deficient in GJIC and have AIG. While applicant does not wish to be bound to any theory, these observations suggest that the origin of human breast carcinomas is the luminal epithelial cell or its precursor cell and that the Type I cells described might be the major target cell for neoplastic transformation.

It should also be noted that SV40 transfected Type I cell clones (extended life or immortal) were shown to be non-tumorigenic when inoculated into athymic nude mice. However, one Type I cell-derived SV40 transfected extended life clone (M11SV-1) was treated with a combination of BrdU and black light, a potent mutagenic treatment (27). An immortal cell line has been obtained from this treatment and this cell line has been shown to be weakly tumorigenic in athymic nude mice. Infection of the BrdU/black light immortalized cell line with a mutated rat neu-oncogene (28) greatly enhanced the tumorigenicity of these cells upon inoculation into athymic nude mice (29).

Cancer cells are believed to arise from stem cells or early precursor cells and often have a phenotype similar to normal undifferentiated cells (30) or have a combined phenotype of different cell types of a common lineage (e.g., leukemia cells often express both lymphoid and myeloid cell antigens) (31). Therefore, cancer has been termed a disease of the pluripotent stem cell (31), a disease of cell differentiation (32) or oncogeny as blocked or partially blocked ontogeny (33). For human tissues, except for peripheral blood stem cells (34), stem cells of solid tissues have rarely been characterized. Attempts to characterize subpopulations of cells with stem cell characteristics in solid tissues have been reported for fetal kidney epithelial cells (35) and for epidermal cells (36). The phenotype of Type I cells herein is suggestive of the presence of stem cells in the Type I cell population as some of them have the ability to give rise to the other type of cells with a different phenotype, i.e. Type I cell (expresses luminal epithelial cell markers) to Type II cell (expresses basal epithelial cell markers). In addition, Type I cells are efficient in GJIC. GJIC deficiency has been reported to be a characteristic of putative stem cells (35).

The results show that two types of HBEC were derived from and cultured from human breast reduction mammoplasty. Type I cells have antigenic characteristics of luminal epithelial cells while Type II cells have antigenic characteristics of basal epithelial cells. Importantly, these two types of cells differ substantially in their response to an oncogenic (SV40) stimulus, i,e. the Type I cells have a greater tendency to become immortal, and most strikingly, have the ability to grow in soft agar (AIG); SV40 transfected Type II cells totally lack the ability to grow in soft agar (AIG⁺). The ability to separate HBEC into cell types that vary in their sensitivity to oncogenic stimuli will facilitate the ability to consistently and reproducibly transform normal HBEC by oncogenic agents.

Figure 1B:
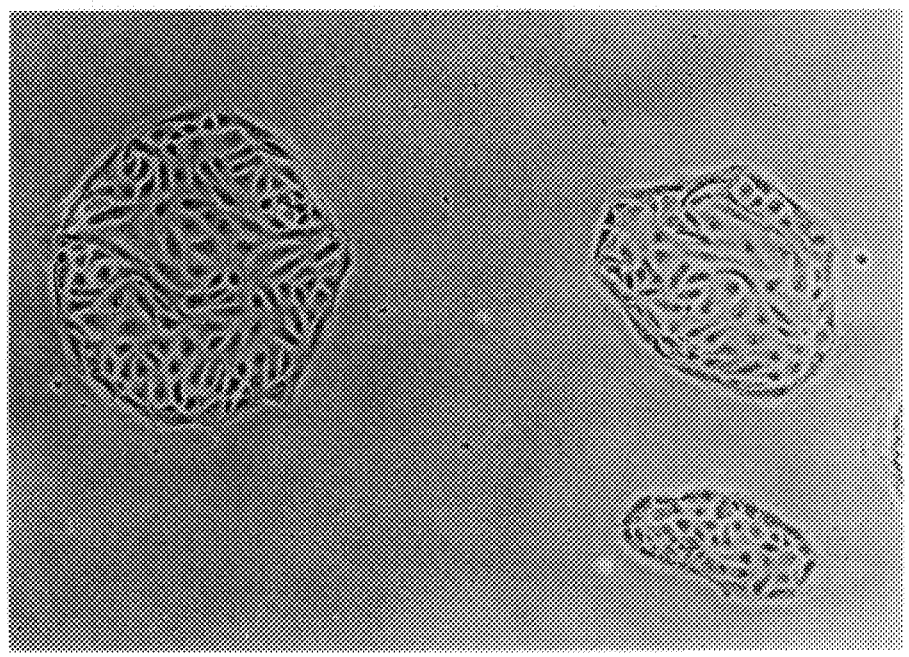

Details as to the Figures are as follows:

FIG. 1: Representative first passage of HBEC in MSU-1 medium for 5 days (X~90). Both Type I (A right, and B) and Type II (A-left) colonies developed in this medium.

Figure 2A:
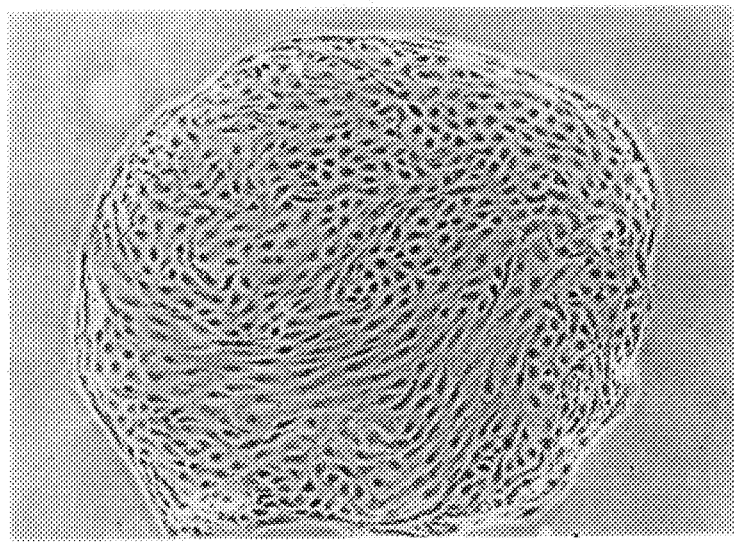
FIGS. 2A–2C are photograph of the cells of the present invention (A and C-right) while the prior art (B and C-left) is shown to be derived from the present invention.
Figure 2B:
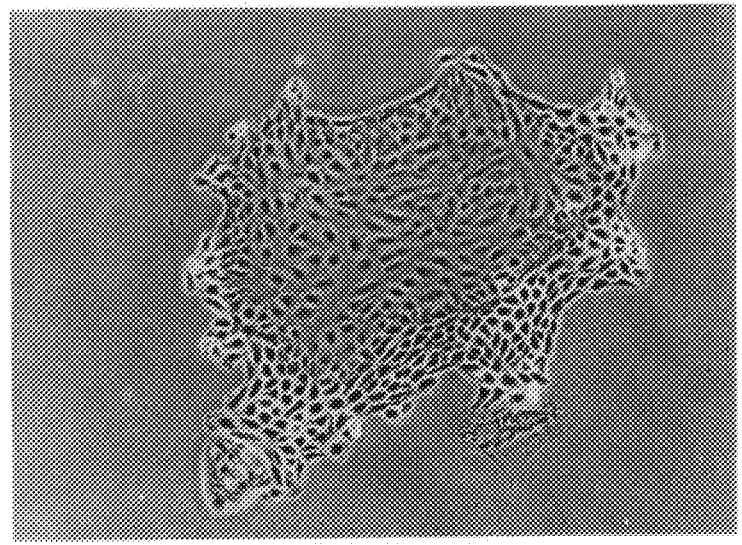
Figure 2C:
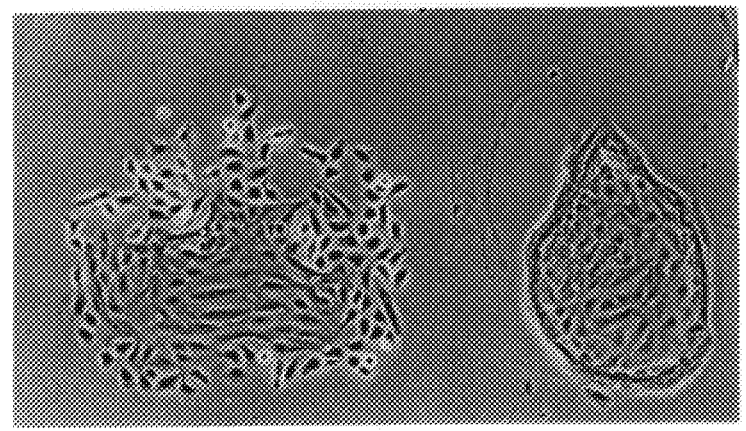

FIG. 2: HBEC colonies grown in MSU-1 medium for 8 days (X~90). One type of colony contains only Type I cells (A and C-right), the other colonies contain both Type I and Type II cells (B and C-left). In these latter colonies, the Type I cells were either partially or completely surrounded by Type II cells.

FIG. 3: Representative gap junctional intercellular communication (GJIC) in Type I and Type II HBEC as examined by the scrape loading/dye transfer technique. Type I cells were deficient in GJIC (A). Type II cells were efficient in GJIC (B) (X~90).

FIG. 4: Representative expression of EMA (top), keratin 18 (middle) and keratin 14 (bottom) in Type I (left) and Type II (right) HBEC as revealed by immunofluorescence staining and detected by the ACAS-570 laser cytometer. (X~200).

FIG. 5: Representative immunofluorescence staining of Type I (A,B) and Type II (C,D) HBEC using antibodies against α6 integrin (A,C) and β4 integrin (B,D). (X~200).

FIG. 6: Representative immunofluorescent staining of SV40 transfected Type I HBEC (B) and SV40 transfected Type II HBEC (D). Non-transfected parental Type I HBEC (A) and Type II HBEC (C) did not show staining. (X~200).

FIG. 7: Representative anchorage independent growth (AIG) of SV40 transfected Type I HBEC (A, X~36) (B, X~90).

While the forms of the invention herein disclosed constitute presently preferred embodiments, many others are possible. It is not intended herein to mention all of the possible equivalent forms or ramifications of the invention. It is understood that the terms used herein are merely descriptive rather than limiting, and that various changes may be made without departing from the spirit or scope of the invention.

REFERENCES

1. Taylor-Papadimitriou, J., Stampfer, M., Bartek, J., Lewis, A., Boshell, M., Lane, E. B., and Leigh, I. M. (1989), "Keratin Expression in Human Mammary Epithelial Cells Cultured From Normal and Malignant Tissue: Relation to in vivo Phenotypes and Influence of Medium", J. CELL SCI., 94:403–413.
2. O'Hare, M. J., Ormerod, M. G., Monaghan, P., Lane, E. B., and Gusterson, B. A. (1991), "Characterization in vitro of Luminal and Myoepithelial Cells Isolated From the Human Mammary Gland By Cell Sorting", DIFFERENTIATION, 46:209–221.
3. Koukoulis, G. K., Virtanen, I., Korhonen, M., Laitinen, L., Quaranta, V., and Gould, V. E. (1991), "Immunohistochemical Localization of Integrins in the Normal, Hyperplastic, and Neoplastic Breast", AM.J. PATHOL., 139:787–799.
4. Trask, D. K., Band, V., Zajchowski, D. A., Yaswen, P., Suh, T., and Sager, R. (1990), "Keratins as Markers That Distinguish Normal and Tumor-Derived Mammary Epithelial Cells", PROC. NATL. ACAD. SCI. U.S.A., 87:2319–2323.
5. Hammond, S. L., Ham, R. G., and Stampfer, M. R. (1984), "Serum-Free Growth of Human Mammary Epithelial Cells: Rapid Clonal Growth in Defined Medium and Extended Serial Passage With Pituitary Extract", PROC. NATL. ACAD. SCI. U.S.A., 81:5435–5439.
6. Band, V., and Sager, R. (1989), "Distinctive Traits of Normal and Tumor-Derived Human Mammary Epithelial Cells Expressed in a Medium That Supports Long-Term Growth of Both Cell Types", PROC. NATL. ACAD. SCI. U.S.A., 86:1249–1256.
7. Chang, C. C., Boezi, J. A., Warren, S. T., Sabourin, C. L., Liu, P. K., Glatzer, L., and Trosko, J. E. (1981), "Isolation and Characterization of a UV-Sensitive Hypermutable Aphidicolin-Resistant Chinese Hamster Cell Line", SOMATIC CELL GENET., 7:235–253.
8. Boyce, S. T., and Ham, R. G. (1983), "Calcium-Regulated Differentiation of Normal Human Epidermal Keratinocytes in Chemidally Defined Clonal Culture and Serum-Free Serial Culture", J. INVEST. DERMAT., 81:33S–40S.
9. Pittelkow, M. R., and Scott, R. E. (1986), "New Techniques for the in vitro Culture of Human Skin Keratinocytes and Perspectives on Their Use for Grafting of Patients With Extensive Burns", MAYO CLINC PROC., 61:771–777.
10. Liebert, M., Wedemeyer, G., Stein, J. A., Washington, R. W., Waes, C. V., Carey, T. E., and Grossman, H. B. (1993), "The Monoclonal Antibody BQ16 Identifies the α6β4 Integrin on Bladder Cancer", HYBRIDOMA, 12:67–80.
11. El-Fouly, M. H., Trosko, J. E., and Chang, C. C. (1987), "Scrape-Loading and Dye Transfer: A Rapid and Simple Technique to Study Gap Junctional Intercellular Communication", EXP. CELL RES., 168:422–430.
12. Bailey, N. T. J. (1959), "Simple Significance Tests Based on the Normal Distribution", In: Statistical Methods in Biology, pp. 33–42, THE ENGLISH UNIVERSITIES PRESS LTD., London.
13. Chang, S. E., Keen, J., Lane, E. B., and Taylor-Papadimitriou, J. (1982), "Establishment and Characterization of SV40-Transformed Human Breast Epithelial Cell Lines", CANCER RES., 42:2040–2053.
14. Stampfer, M. R., and Bartley, J. C. (1985), "Induction of Transformation and Continuous Cell Lines From Normal Human Mammary Epithelial Cells After Exposure to Benzo [a]pyrene", PROC. NATL. ACAD. SCI. U.S.A., 82:2394–2398.
15. Band, V., Zajchowski, D., Kulesa, V., and Sager, R. (1990), "Human Papilloma Virus DNAs Immortalize Normal Human Mammary Epithelial Cells and Reduce Their Growth Factor Requirements", PROC. NATL. ACAD. SCI. U.S.A., 87:463–467.
16. Rudland, P. S., Ollerhead, G., and Barraclough, R. (1989), "Isolation of Simian Virus 40-Transformed Human Mammary Epithelial Stem Cell Lines That Can Differentiate To Myoepithelial-like Cells in Culture and in vivo", DEVELOPMENTAL BIOLOGY, 136:167–180.
17. Bartek, J., Bartkova, J., Lalani, E-N., Brezina, V., and Taylor-Papadimitriou, J. (1990), "Selective Immortalization of a Phenotypically Distinct Epithelial Cell Type by Microinjection of SV40 DNA into Cultured Human Milk Cells", INT. J. CANCER, 45:1105–1112.
18. Garcia, I., Brandt, D., Weintraub, J., Zhou, W., and Aapro, M. (1991), "Loss of Heterozygosity for the Short Arm of Chromosome 11(11p15) in Human Milk Epithelial Cells Immortalized by Microinjection of SV40 DNA. CANCER RES., 51:294–300.
19. Bartek, J. Bartkova, J., Kyprianou, N., Lalani, E-N., Staskova, Z., Shearer, M., Chang, S., and Taylor-Papadimitriou, J. (1991), "Efficient Immortalization of Luminal Epithelial Cells From Human Mammary Gland By Introduction of Simian Virus 40 Large Tumor Antigen with a Recombinant Retrovirus", PROC. NATL. ACAD. SCI. U.S.A., 88:3520–3524.
20. Berthon, P., Goubin, G., Dutrillaux, B., Degeorges, A., Faille, A., Gespach, C., and Calvo, F. (1992), "Single-step Transformation of Human Breast Epithelial Cells by SV40 Large T Oncogene", INT. J. CANCER, 52:92–97.
21. Van Der Haegen, B. A., Shay, J. W. (1993), "Immortalization of Human Mammary Epithelial Cells by SV40 Large T-antigen Involves a Two Step Mechanism", IN VITRO CELL. DEVE. BIOL., 29A:180–182.
22. Shay, J. W., Van Der Haegen, V. A., Ying, Y., and Wright, W. E. (1993), "The Frequency of Immortalization of 23. Hamburger, A. W., and Salmon, S. E. (1977), "Primary Bioassay of Human Tumor Stem Cells", SCIENCE, 197:461–463.
24. Stoker, Mr. (1968), "Abortive Transformation by Polyoma Virus", NATURE, 218:234–238.
25. Macpherson, I. A. (1973), "Soft Agar Techniques", In: P. F. Kruse, and M. K. Patterson (eds.), Tissue Culture Methods and Applications, pp. 267–273, NEW YORK: ACADEMIC PRESS.
26. Marshall, C. J., Franks, L. M., and Carbonell, A. W. (1977), "Markers of Neoplastic Transformation in Epithelial Cell Lines Derived From Human Carcinomas", J. NATL. CANCER INST., 58:1743–1751.
27. Chu, E. H. Y., Sun, N. C., and Chang, C. C. (1972), "Induction of Auxotrophic Mutations by Treatment of Chinese Hamster Cells With 5-Bromodeoxyuridine and Black Light", PROC. NATL. ACAD. SCI U.S.A., 69:3459–3463.
28. Dotto, G. P., Moellmann, G., Ghosh, S., Edwards, M., and Halaban, R. (1989), "Transformation of Murine Melanocytes by Basic Fibroblast Growth Factor cDNA and Oncogenes and Selective Suppression of the Transformed Phenotype in a Reconstituted Cutaneous Environment", J. CELL BIOL., 109:3115–3128.
29. Kao, C. Y., Oakley, C. S., Welsch, C. W., and Chang, C. C., "Characterization of Two Types of Normal Human Breast Epithelial Cells Derived From Reduction Mammoplasty: Growth Requirements in Defined Culture Media and Neoplastic Transformation". Submitted for publication.
30. Sigal, S. H., Brill, S., Fiorino, A. S., and Reid (1992), L. M. "The Liver as a Stem Cell and Lineage System", AM. J. PHYSIOL., 263:G139–G148.
31. Sawyers, C. L., Denny, C. T., andwitte, O. N. (1991), "Leukemia and the Disruption of Normal Hematopoiesis", CELL, 64:337–350.
32. Markert, C. L. (1968), "Neoplasia: A Disease of Cell Differentiation", CANCER RES., 28:1908–1914.
33. Potter, V. R. (1978), "Phenotypic Diversity in Experimental Hepatomas: The Concept of Partially Blocked Ontogeny", BR. J. CANCER, 38:1–23.
34. Gabbianelli, M., Sargiacomo, M., Pelosi, E., Testa, U., Isacchi, G., and Peschle, C. (1990), "Pure Human Hematopoietic Progenitors: Permissive Action of Basic Fibroblast Growth Factor", SCIENCE, 249:1561–1564.
35. Chang, C. C., Trosko, J. E., El-Fouly, M. H., Gibson-D'Ambrosio, R. E., and D'Ambrosio, S. M. (1987), "Contact Insensitivity of a Subpopulation of Normal Human Fetal Kidney Epithelial Cells and of Human Carcinoma Cell Lines", CANCER RES., 47:1634–1645.
36. Jones, P. H., and Watt, F. M. (1993), "Separation of Human Epidermal Stem Cells From Transit Amplifying Cells on the Basis of Differences in Integrin Function and Expression", CELL, 73:713–724.
37. Potten, C. S. and Loeffler, M. (1990), "Stem Cells: Attributes, Cycles, Spirals, Pitfalls and Uncertainties, Lessons For and From The Crypt", DEVELOPMENT, 110:1001–1020.
38. Sloane, J. and Ormerod, M. G. (1981), "Distribution of Epithelial Membrane Antigen in Normal and Neoplastic Tissues and its Value in Diagnostic Tumor Pathology", CANCER, 47:1786–1795.

What is claimed is:

1. A substantially purified human breast epithelial cell comprised of the following characteristics:
   cell morphology: variable in shape;
   colony morphology: boundary smooth; and
   when subjected to growth in a medium comprised of fetal bovine serum, the cell has the following expression of:
   epithelial membrane antigen: positive;
   keratin 18: positive; and
   keratin 14: negative.

2. A substantially purified human breast epithelial stem cell comprised of the following characteristics:
   cell morphology: variable in shape;
   colony morphology: boundary smooth; and
   when subjected to growth in a medium comprised of fetal bovine serum, the cell has the following expression of:
   epithelial membrane antigen: positive;
   keratin 18: positive; and
   keratin 14: negative.

3. The cell of claims 1 or 2 further characterized as having a delayed adhesion to plastic after trypsinization and subculture.

4. The epithelial cell of claim 1 is further characterized as having a positive response to immunoclonal antibodies against keratin 18 and not having a positive response to immunoclonal antibodies against keratin 14.

5. The epithelial cell of claim 2 being further characterized as being converted from a cell morphology variable in shape to a cell morphology uniform in shape and a colony morphology of smooth boundary to a colony morphology of boundary not smooth by subjecting the cell to cholera toxin.

6. A method of obtaining the cell of claim 1 comprising the steps of:
   a) providing a mixture of cells;
   b) subjecting the cells to a culture medium comprised of a mixture of Eagle's MEM, epidermal growth factor, insulin, hydrocortisone, transferrin, triiodothyronine, estradiol, vitamins, and amino acids;
   c) separating the cells; and
   d) recovering the desired cells.

7. A method of obtaining the epithelial stem cell of claim 2 comprising the steps of:
   a) providing a mixture of cells;
   b) subjecting the cells to a culture medium comprised of a mixture of Eagle's MEM, MCDB 153, epidermal growth factor, insulin, hydrocortisone, transferrin, triiodothyronine, estradiol, vitamins, and amino acids;
   c) separating the cells; and
   d) recovering the desired cells.

8. The method of claims 6 or 7 wherein the cells are subjected to trypsinization and subculture in the presence of a plastic substrate whereby the desired epithelial cell remains in the liquid phase.

9. The method of claim 8 wherein the cell desired to be separated is suspended in the liquid phase and is obtained from the liquid phase.

10. The method of claims 6 or 7 wherein after the cells are subjected to the culture medium,
    promoting growth of the cell by adding an effective growth promoting amount of fetal bovine serum, and also inhibiting the growth of undesired epithelial cell types.

11. A culture medium for culturing a human breast epithelial cell comprised of a mixture of Eagle's MEM, epidermal growth factor, insulin, hydrocortisone, transferrin, triiodothyronine, estradiol, vitamins, and amino acids.

12. A medium comprising a mixture of Eagles'MEM and MCDB 153 medium supplemented with human recombinant epidermal growth factor, insulin, hydrocortisone, human transferrin, triiodothyronine and 17-$\beta$ estradiol in the absence of prostaglandin $E_1$, ovine prolactin, bovine pituitary extract and cholera toxin.

* * * * *